(12) United States Patent
Monagle

(10) Patent No.: US 6,797,309 B2
(45) Date of Patent: Sep. 28, 2004

(54) SOY PROTEIN PRODUCT AND PROCESS FOR ITS MANUFACTURE

(75) Inventor: Charles W. Monagle, Fort Wayne, IN (US)

(73) Assignee: Solae, LLC, St. Louis, MO (US)

( * ) Notice: Subject to any disclaimer, the term of this patent is extended or adjusted under 35 U.S.C. 154(b) by 325 days.

(21) Appl. No.: 09/930,733

(22) Filed: Aug. 15, 2001

(65) Prior Publication Data

US 2002/0039619 A1 Apr. 4, 2002

Related U.S. Application Data

(60) Provisional application No. 60/226,706, filed on Aug. 18, 2000.

(51) Int. Cl.$^7$ .............................. A23L 1/20; A23L 2/00
(52) U.S. Cl. ...................... 426/590; 426/634; 426/656; 426/800; 426/801; 530/378
(58) Field of Search .......................... 530/378; 426/634, 426/656, 590, 800, 801

(56) References Cited

U.S. PATENT DOCUMENTS

| | | | |
|---|---|---|---|
| 4,431,737 A | | 2/1984 | Olivieri et al. |
| 5,710,365 A | * | 1/1998 | Kerr et al. .................. 800/263 |
| 5,858,449 A | | 1/1999 | Crank et al. |
| 5,936,069 A | | 8/1999 | Johnson |

FOREIGN PATENT DOCUMENTS

| | | |
|---|---|---|
| EP | 0 479 596 A1 | 4/1992 |
| GB | 1348205 | 3/1974 |
| WO | WO 95/27406 | 10/1995 |
| WO | WO 02/15712 | 2/2002 |

OTHER PUBLICATIONS

International search report mailed Mar. 14, 2002.
XP002191359—Article "Soybean Utilization" 1987, pp 58–59.
XP001061292—Article "Enzymatic degradation of oligosaccharides in soybean flours", Food Chemistry 1997, vol. 59, No. 2, pp 279–282.
XP000952652—Article "Hydrolysis of alpha–galactosyl oligosaccharides in soymilk by alpha–d–galactosidae of bifidobacterium breve 203" Agricultural and Biological Chemistry, vol. 51, No. 2 1987 pp315–322.
XP002191360—Database FSTA Online, International Food Information Service, "Utilization of enzymes in the manufacture of soy milk and by–products" 1995.
XP002191361—Database FSSTA Online, International Food Information Service, "Low–oligosaccharide soy milk: application of alpha–galactosidase for hydrolysing soy–oligosaccharide" 1991.

* cited by examiner

*Primary Examiner*—Anthony Weier
(74) *Attorney, Agent, or Firm*—James L. Cordek

(57) ABSTRACT

This invention relates to a soy protein product with a modified sugar profile. The soy protein product has desirable flavor and functional properties. The soy protein product has a high sucrose and monosaccharide content and is low in indigestible oligosaccharides. The soy protein product does not have galactinol that is present in soybeans developed to have a low indigestible oligosaccharide content. The soy protein product is rich in isoflavones. The method for manufacturing the soy protein product uses conventional soybeans that have better agronomic properties than soybeans developed to have a low indigestible oligosaccharide content. The method for manufacturing the soy protein product uses a α-galactosidase enzyme. The method for manufacturing the soy protein product retains the natural level of isoflavones occurring in soybeans.

10 Claims, 2 Drawing Sheets

SOY PROTEIN PRODUCT AND PROCESS FOR ITS MANUFACTURE

CROSS REFERENCE TO RELATED APPLICATIONS

This filing claims the benefit of U.S. Provisional Patent Application No. 60/226,706, filed Aug. 18, 2000.

FIELD OF THE INVENTION

This invention relates to a soy protein product with a modified sugar profile. The soy protein product has desirable flavor and functional properties. The soy protein product has a high sucrose and monosaccharide content and is low in indigestible oligosaccharides. The soy protein product does not have galactinol that is present in soybeans developed to have a low indigestible oligosaccharide content. The soy protein product is rich in isoflavones. The method for manufacturing the soy protein product uses conventional soybeans that have better agronomic properties than soybeans developed to have a low indigestible oligosaccharide content. The method for manufacturing the soy protein product uses a α-galactosidase enzyme. The method for manufacturing the soy protein product retains the natural level of isoflavones occurring in soybeans.

BACKGROUND OF THE INVENTION

This invention relates to a soy protein product. The benefits of soy protein are well documented.

Cholesterol is a major concern with consumers throughout the industrialized world. It is well known that vegetable products contain no cholesterol. For decades, nutritional studies have indicated that the inclusion of soy protein in the diet actually reduces serum cholesterol levels in people who are at risk. The higher the cholesterol, the more effective soy proteins are in lowering that level.

Soybeans have the highest protein content of all cereals and legumes with around 40% protein while other legumes have 20–30%, whereas cereals have about 8–15% protein. Soybeans also contain about 20% oil and the remaining dry matter is mostly carbohydrate (35%). On a wet basis (as is), soybeans contain about 35% protein, 17% oil, 31% carbohydrates and 4.4% ash.

In the soybean, both storage protein and lipid bodies are contained in the usable meat of the soybean (called the cotyledon). The complex carbohydrate (or dietary fiber) is also contained in the cell walls of the cotyledon. The outer layer of cells (called the seed coat) makes up about 8% of the soybean's total weight. The raw, dehulled soybean is, depending on the variety, approximately 18% oil, 15% soluble carbohydrates, 15% insoluble carbohydrates, 14% moisture and ash and 38% protein.

In processing, soybeans are carefully selected for color and size. The soybeans are then cleaned, conditioned (to make removal of the hull easier) and cracked, dehulled and rolled into flakes. The flakes are subjected to a solvent bath that removes the oil. The solvent is removed and the flakes are dried, creating the defatted soy flakes that are the basis of all soy protein products. Despite the large number of products on the market, there are only three types of soy protein: flours, isolates and concentrates.

Soy flours are the simplest forms of soy protein with a protein content of approximately 50%. Simply grinding and screening the defatted flakes produces soy flours.

Soy flours are high in oligosaccharides, the soluble carbohydrates that give soy flours the "beany" flavor that some people find objectionable. The simple processing leaves the soy flour with many of the soybean's characteristics. The lack of processing also makes soy flours highly variable in terms of quality.

Soy flours and grits are still widely produced and are used most often in baked goods, snack foods and pet foods applications where the high flavor profile does not pose a problem. Textured soy flours were an early attempt at simulating or enhancing the texture of meat products. Texturizing does not change the composition of soy flours and reduces the flavor profile only slightly. Their primary applications are inexpensive meat products or pet foods.

The oligosaccharides raffinose and stachyose in soy flour potentially cause flatulence as their bacterial fermentation in the colon creates intestinal gas. Suarez reported that ingestion of 34 grams (g) of conventional soy flour (1.3 g raffinose and stachyose) caused no significant increase in flatulence frequency, whereas ingestion of 80 g of conventional soy flour (3.1 g raffinose and stachyose) resulted in a significant increase in flatulence frequency. "Gas Production in Humans Ingesting a Soybean Flour Derived from Beans Naturally Low in Oligosaccharides," Suarez, Fabrizis L. et al., *Am. J. Clin. Nutr.*, 69:135–9 (1999).

The prior art describes methods for reducing the oligosaccharide content of soy milk and soy flour. Crocco describes using α-galactosidase from microbial or fungal sources as a means for pre-digesting oligosaccharides in soy milk. "Treatment of Soy Milk Oligosaccharides by a Homogeneric Enzyme Extract Containing α-Galactosidase," Crocco, Stephanie Carmela, The Louisiana State University and Agricultural and Mechanical College (1973); *Food Technology*, Order No. 74-18, 329. Mulimani describes attempting to use a crude preparation of α-galactosidase from guar to degrade oligosaccharides present in soybean flours. "Enzymatic Degradation of Oligosaccharides in Soybean Flours," Mulimani, H. V. et al., *Food Chemistry*, Vol. 59, No. 2, pp. 279–282 (1997). Ultrafiltration has also been employed to remove the oligosaccharides from soy milk.

Isolates are produced through standard chemical isolation, drawing the protein out of the defatted flake through solubilization (alkali extraction at pH 7–10) and separation followed by isoelectric precipitation. As a result, isolates are 90% protein on a moisture-free basis. Isolates can be made with a high percentage of soluble protein and a low flavor profile. They contain no dietary fiber and are sometimes high in sodium, properties that can limit their application. Isolate processing is relatively complex and much of the soybean's protein is lost in the centrifuging process, so the cost of isolates is high. Their major applications have been in dairy substitution, as in infant formulas and milk replacers.

Soy concentrates have at least 65% protein and typically have about 70% protein. A myriad of applications has been developed for soy concentrates and texturized concentrates in processed foods' meat, poultry, fish, cereal and dairy systems.

Removing soluble carbohydrate material from defatted soy meal makes soy protein concentrates. Aqueous alcohol extraction (60–80% ethanol) or acid leaching (isoelectric pH 4.5) is the most common means for carbohydrate removal.

The prior art describes soy protein products made from low oligosaccharide soybeans. In U.S. Pat. No. 5,858,449, Crank describes a process for making a soy protein product that has at least 60% protein and 10% sucrose and less than 4% dietary fiber and 1.5% stachyose. In U.S. Pat. No. 5,936,069, Johnson describes a process for making a soy protein product having at least 60% protein and less than 3% stachyose, 1% raffinose and 0.5% fiber. Crank uses soybeans that have a low stachyose content due to mutagenesis techniques. Johnson uses soybeans genetically modified to have a low raffinose and stachyose content.

It is an object of this invention to make a novel, soy protein product with a modified sugar profile from soybeans conventionally grown by farmers and used by soybean processors. The modified sugar profile results in desirable flavor and functional properties.

It is further an object of this invention to produce a soy protein product with a desired level of sucrose. A high sucrose content gives the soy protein product advantages of sweetness and nonbrowning over conventional soy.

It is further an object of this invention to produce a soy protein product with a combined sucrose and monosaccharide content as great as the sucrose content of products made from low oligosaccharide soybeans. Monosaccharide is similar to sucrose in sweetness.

It further is an object of this invention to produce a soy protein product that is low in indigestible oligosaccharides. It is further an object of this invention to be able to control the manufacturing process to achieve a desired, reduced oligosaccharide content.

It was discovered that the sucrose and indigestible oligosaccharide content of the soy protein product can be controlled by using a single activity enzyme that hydrolyses only stachyose and raffinose to generate galactose and sucrose. The prior art does not teach a soy protein product made from conventional soybeans. The prior art also does not teach using an enzymatic process to make a soy protein product.

It is further an object of this invention to make a soy protein product by an economically efficient method. The low oligosaccharide soybeans used by Crank and Johnson tend to have poorer agronomic properties than conventional soybeans. Agronomic properties include germination and seedling development, growing and maturity, nitrogen fixation, disease and pest resistance and yield. The low oligosaccharide soybeans used by Crank and Johnson also would have higher harvesting, drying, storage, marketing, trading, handling and processing costs because the soybeans must be segregated and identity preserved.

It is further an object of this invention to make a soy protein product that does not contain galactinol. The low oligosaccharide soybeans used by Crank and Johnson contain galactinol. Suarez reported that the low oligosaccharide soy flour had about 2.2% galactinol, whereas soy flour from conventional soybeans had none, as conventional soybeans do not contain a detectable amount of galactinol. It is believed that galactinol, a precursor in raffinose and stachyose synthesis, also would cause intestinal gas by fermentation in the colon. Therefore, the potential digestibility benefits of low oligosaccharide soybeans might be negated by the presence of galactinol in that soybean.

It is further an object of this invention to produce a soy protein product that is rich in isoflavones. In recent years, isoflavones have been researched extensively to better understand their role in chronic disease prevention. The American Institute for Cancer Research says isoflavones "may inhibit enzymes necessary for the growth and spread of many types of cancer," such as breast cancer, prostate cancer and colon cancer. And isoflavones are also showing great promise in preventing osteoporosis and treating menopausal symptoms. Isoflavones are largely unaffected by the invention's water extraction process. Therefore, they are retained in the invention at naturally occurring levels found in soybeans.

It is further an object of this invention to produce a soy protein product containing significant amounts of calcium, magnesium, phosphorus, potassium and amino acids. These nutritional constituents are largely unaffected by the invention's water extraction process. Therefore, they are retained in the invention at naturally occurring levels found in soybeans.

SUMMARY OF THE INVENTION

The present invention comprises a soy protein product having (a) at least 60% protein of total dry matter; (b) a combined sucrose and monosaccharide content of at least 10% of total dry matter and (c) less than about 5% indigestible oligosaccharides of total dry matter and (d) being substantially free of galactinol. In another embodiment, this invention concerns a method for manufacturing a protein product comprising: (a) providing a substantially defatted soybean material; (b) treating said material with an enzyme at an effective temperature and pH for an effective time to achieve a combined sucrose and monosaccharide content of at least 10% of total dry matter in said product and less than 5% indigestible oligosaccharides of total dry matter in said product; (c) removing fiber from said material before or after said treatment to achieve at least 60% protein of total dry matter in said product and (d) inactivating said enzyme after said treatment. The product is then used in a liquid or dry beverage, food or nutritional product.

DETAILED DESCRIPTION OF THE INVENTION

Figure 1:
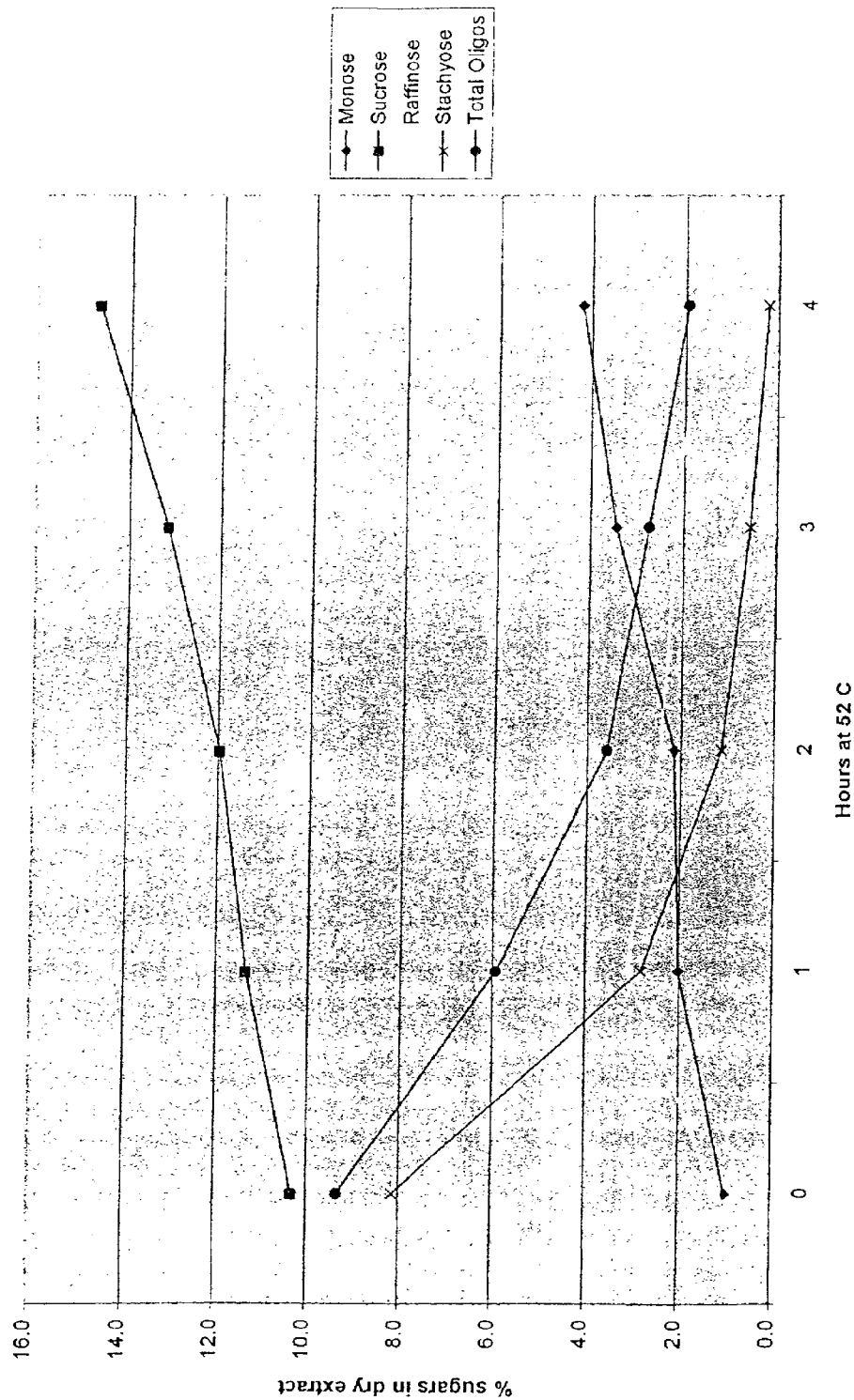
FIG. 1 depicts the effects of a $\alpha$-glycosidase enzyme, namely a $\alpha$-galactosidase enzyme with no invertase activity, on the sugars of soy flour extract over time. Sucrose can be increased to over 14%. Stachyose can be reduced to about 0.2%. Total indigestible oligosaccharides can be reduced to less than 2%. Raffinose initially increases to about 3% after 1 hour, but then decreases to about 2% after 3 hours. The monosaccharide content is more than doubled.

The present invention comprises a soy protein product having (a) at least 60% protein of total dry matter; (b) a combined sucrose and monosaccharide content of at least 10% of total dry matter and (c) less than about 5% indigestible oligosaccharides of total dry matter and (d) being substantially free of galactinol. In another embodiment, this invention concerns a method for manufacturing a protein product comprising: (a) providing a substantially defatted soybean material; (b) treating said material with an enzyme at an effective temperature and pH for an effective time to achieve a combined sucrose and monosaccharide content of at least 10% of total dry matter in said product and less than 5% indigestible oligosaccharides of total dry matter in said product; (c) removing fiber from said material before or after said treatment to achieve at least 60% protein of total dry matter in said product and (d) inactivating said enzyme after said treatment. The product is then used in a liquid or dry beverage, food or nutritional product.

The subject method invention generally includes: 1) dehulling whole soybeans; 2) flaking the dehulled soybeans; 3) extracting soybean oil from the flaked soybeans with hexane, a solvent; 4) desolventizing the defatted soybean flakes without high heating or toasting to produce "white" flakes; 5) grinding the flakes to make soy flour; 6) removing fiber from the soy flour and hydrolyzing stachyose and raffinose in the soy flour with an enzyme and then inactivating the enzyme 7) separating the slurry into a liquor and a cake and 8) drying the liquor. Steps 1 through 4 described above is commonly referred to as the extraction process for soybeans. The general procedure for the above-described steps 1 through 5 is well understood. U.S. Pat. No. 5,097,017 (Konwinski); U.S. Pat. No. 3,897,574 (Pass); "Extraction of Oil from Soybeans," *J. Am. Oil Chem. Soc.*, 58, 157 (1981) and "Solvent Extraction of Soybeans," *J. Am. Oil Chem. Soc.*, 55, 754 (1978).

The first item described above is dehulling. Dehulling is the process in which the soybean hulls are removed from the whole soybeans. The soybeans are carefully cleaned prior to dehulling to remove foreign matter, so that product will not be contaminated by color bodies. Soybeans also are normally cracked into about 6 to 8 pieces prior to dehulling.

The hull typically accounts for about 8% of the weight of the whole soybean. The dehulled soybean is about 10% water, 40% protein, 20% fat, with the remainder mainly being carbohydrates, fiber and minerals.

The second step described above is the flaking process. Soybeans are conditioned prior to flaking by adjusting moisture and temperature to make the soybean pieces sufficiently plastic. The conditioned soybean pieces are passed through flaking rolls to form flakes about 0.01 to 0.012 inches (in.) thick.

The third step described above is soybean oil removal from the flakes. The soybean flakes are defatted by contacting them with hexane to remove the soybean oil. Soybean oil is used in margarine, shortening and other food products, and is a good source of lecithin, which has many useful applications as an emulsifier.

In the fourth step described above, the hexane-defatted soybean flakes are desolventized—hexane is removed—without toasting to produce white flakes. This is different than conventional soybean oil hexane processes where the flakes are toasted and used for animal feed.

In the fifth step described above, the white flakes are ground to make soy flour. Soy flour that can be used as a starting material for the subject invention is readily, commercially available. Commercial soy flour typically would have at least 50% (52.5%) protein (N×6.25); about 30–40% (34.6%) carbohydrates; about 5–10% (6%) moisture; about 5–10% (6%) ash; about 2–3% (2.5%) crude fiber and less than about 1% (0.9%) fat (ether extract).

In the preferred embodiment of this invention, the soy flour has a protein dispersibility index (PDI) of 90 and is 80 mesh. PDI is determined by American Oil Chemist's Society (AOCS) method Ba 10–65. 90 PDI would be soy flour with no heat treatment that is enzyme active. 80 mesh means that greater than 95% of the soy flour passes through a US standard number 80 sieve.

The next step of the invention involves treating the starting material with an enzyme and removing fiber from the material before or after the enzyme treatment. In either case, the starting material is first preferably slurried with water. In the preferred embodiment of this invention, the water is pre-heated. A suitable temperature is 130 degrees Fahrenheit (° F). In the preferred embodiment of this invention, the slurry is about 10–20% solids.

It also usually is necessary to provide some agitation or mixing to slurry the starting material. One means for performing the mixing is a propeller-type agitator.

The slurry is treated with an enzyme at an effective temperature and pH for an effective time to achieve a combined sucrose and monosaccharide content of at least 10% of total dry matter and less than 5% indigestible oligosaccharides of total dry matter in the soy protein product. FIG. 1 shows the pattern of hydrolysis in the soy sugars is to see decline in stachyose, a temporary increase in raffinose, an increase in sucrose and an increase in free galactose. Raffmose increases because it is produced as an intermediate product faster than it is hydrolyzed.

In the preferred embodiment, the enzyme is a $\alpha$-glycosidase enzyme and most preferred a $\alpha$-galactosidase enzyme with essentially no invertase (sucrase) activity. An example, of the most preferred enzyme is Novo Nordisk A/S Alpha-Gal 1000 and the most preferred effective amount of it is about 450–2300 galactosidase units per pound of starting material, which is about 0.001–0.005 pounds of the enzyme in its liquid form per pound of starting material. The enzyme's activity of galactosidase units per gram is determined by Novo Nordisk's analytical method.

Alpha-Gal 1000 is a single activity enzyme that hydrolyses only stachyose and raffinose to generate galactose and sucrose and the enzyme is effective in the pH range of 3.5–6.5. Another suitable enzyme is a $\alpha$-galactosidase made by the Amano company. Both enzymes will achieve complete conversion of stachyose and raffinose at ambient temperature given time.

In the preferred embodiment of this invention, the effective time is 1–4 hours, most preferred 2–3 hours; the effective temperature is 125–140° F., most preferred 125–130° F. and the effective pH is 6–6.5, most preferred 6–6.3. One means for reaching the effective pH is to adjust the pH of the slurry with hydrochloric acid.

In this invention, the effective time can be controlled to achieve a desired level of indigestible oligosaccharides in the soy protein product. For example, if the effective time with the preferred enzyme is controlled between 1–2 hours, the product can have greater than 1.5% stachyose of total dry matter and less than about 2–3% raffinose of total dry matter.

After the enzyme treatment, the enzyme is deactivated in the method embodiment of this invention. One means for deactivation is pasteurization at 180° F. One means for pasteurization is jet cooking. In yet another embodiment of this invention, the slurry could be held in a steam-jacketed kettle. The enzyme deactivation/pasteurization is performed so that the product also tests negative for salmonella and has an acceptable microbial profile.

Figure 2:
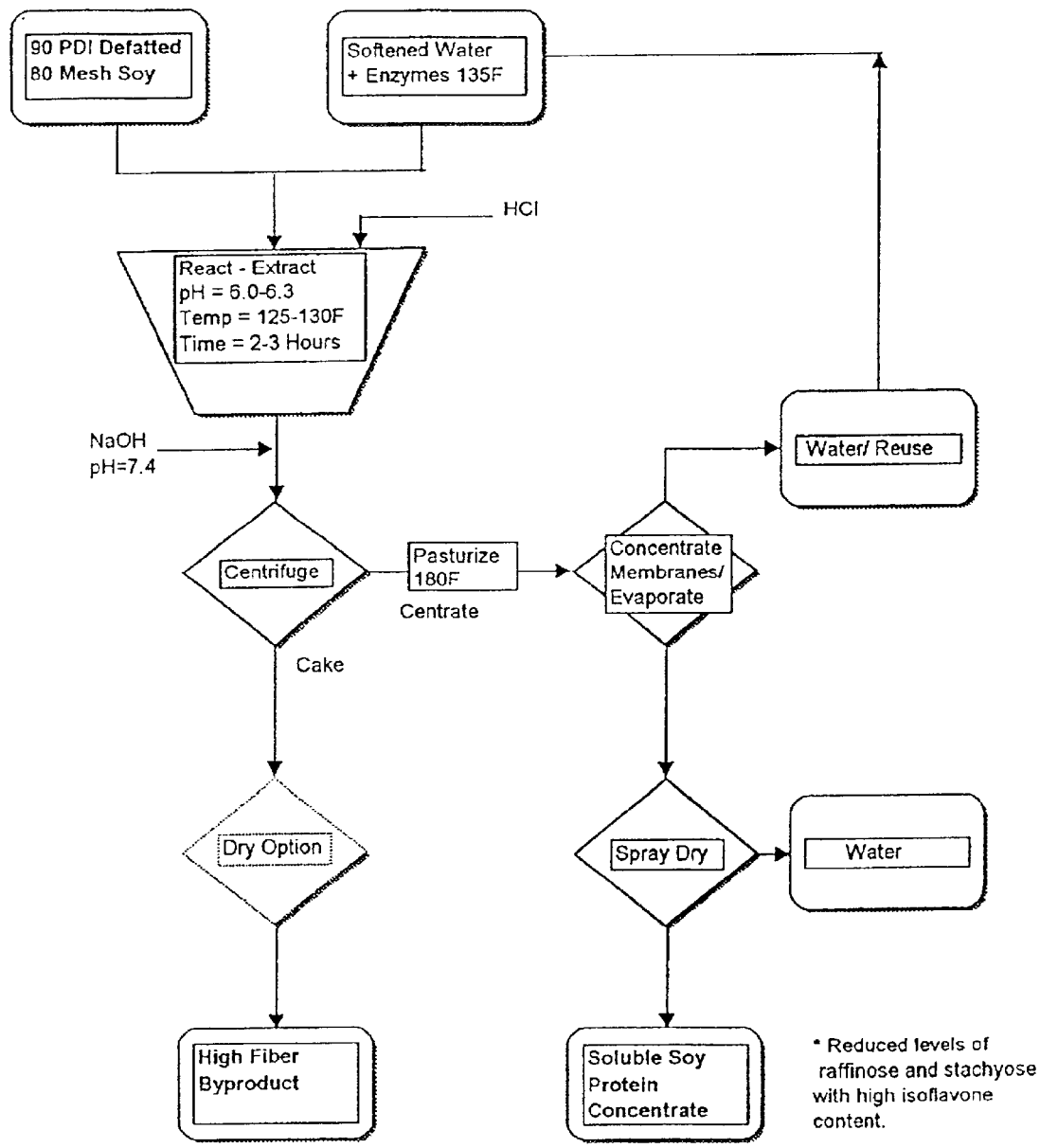
FIG. 2 depicts a generalized representation of one embodiment of the invention. Soy flour is slurried with water, acid and enzyme and reacted for several hours at an elevated temperature. The reacted slurry's pH is adjusted with a base. The pH adjusted, reacted slurry is centrifuged. The centrate is pasteurized, concentrated and dried to form a soy protein product. The cake from the centrifugation is optionally dried to form a high fiber byproduct.

The next operation to be described is fiber removal to achieve at least 60% protein of total dry matter in said product, more preferred 66% protein with about 70% product yield. Again, the fiber removal can occur before or after the enzyme treatment. FIG. 2 shows an embodiment of this invention where the fiber removal occurs after the enzyme treatment and the enzyme is deactivated after the fiber removal.

One means for removing fiber is adjusting the pH of the slurry to about 7–7.5, most preferred 7.4, with sodium hydroxide and separating the slurry to form a cake and a liquor. The separation can be performed by a number of physical separation means; however, centrifugation is the most efficient and effective means. In the preferred embodiment of this invention, a scroll-type centrifuge is used to perform the separation. In yet another embodiment of this invention, the separation can be performed with a disc-type or tubular centrifuge.

The enzyme treated, fiber removed material (the liquor) is dried to form the soy protein product. The preferred means of drying is a vertical spray dryer with a high-pressure nozzle.

The product has many uses. For example, it can be used as a milk replacer and in drink mixes and beverages, such as chocolate, vanilla and pineapple beverages; dairy products, such as fruit yogurt; nutrition and health products, such as protein bars; whole muscle meat injection; surimi products; emulsified meats; cereal products, such as breakfast cereals; bakery products, such as blueberry muffins and other liquid or dry beverage, food or nutritional products.

FIG. 2 shows that the liquor is optionally concentrated after the separation. The concentration may be performed by membrane separation or evaporation unit operations. A benefit of concentrating the liquor prior to drying is that drying costs are reduced.

FIG. 2 shows that the cake is optionally dried to form a high fiber byproduct. The byproduct would have about 20–25% protein.

The dried products may be coated with commercial lecithin or other food-grade surfactants, such as mono-diglycerides, to improve water dispersibility and reduce clumping of the product. Such a coating-addition would be in the range of about 0.5%.

These and other aspects of the present invention may be more readily understood by reference to one or more of the following examples.

EXAMPLE 1

40 grams (g) of soy flour with a 90 protein dispersibility index (PDI) were slurried in 360 g of water and equilibrated to temperature in a 52 degrees Celsius water bath with continuous stirring. The pH of the slurry was measured as 6.5 and was not adjusted further. A control sample was taken then 0.19 g (0.5% of solids) of low side activity α-galactosidase enzyme (Novo Nordisk Alpha-Gal 1000) was added to the slurry. Stirring was continued throughout the process. Samples were taken at 1, 2, 3 and 4 hours. As each sample, including the control sample, was taken it was placed in a 50-milliliter centrifuge tube and immersed in boiling water for 10 minutes (min.) to inactivate the enzyme. The samples were centrifuged for 5 min. at 3000 revolutions per min. then the supernatants were decanted, frozen and freeze-dried. Sugar analysis was conducted on the freezed dried supernatants by the method of Shukla. Fett Wissenschaft Technologie, 89(2), pp. 75–79 (1987).

EXAMPLE 2

519 pounds (lbs.) of water were added to a mixing tank at 130 degrees Fahrenheit (° F.). 50 lbs. of soy flour were added. The pH was adjusted to 6.2 with hydrochloric acid. 113.5 grams (g) of Novo Nordisk Alpha-Gal 1000 enzyme were added. The slurry was mixed for 3 hours (hrs.) at 130° F. The pH of the enzyme treated slurry was adjusted to 7.4 with 50% sodium hydroxide. The enzyme treated, pH adjusted slurry was fed at the rate of one gallon per minute (GPM) to a Sharples scroll-type centrifuge. The liquor (6.90% solids) was jet cooked at 4 GPM at 220° F. The jet-cooked liquor was spray dried using a high pressure pump feeding a spray nozzle. The dryer's outlet temperature was 195° F. The spray drying of the jet cooked liquor yielded 24.1 lbs. of a soy protein product. The centrifuged cake was re-diluted and spray dried to make a high fiber co-product.

The soy protein product has 4.99% moisture (95.01% dry matter); 9.92% nitrogen (7.88% nitrogen suspension; 79.44 nitrogen solubility index); 61.99% crude protein; 0.4% crude fiber; 0.22% crude fat and 8.24% ash. The product has 15.9% total sugars (159.8 milligrams (mg)/g); 2.8% indigestible oligosaccharides (28.44 mg/g); 2.2% monosaccharides (22.06 mg/g); 0.3% fructose; 0.3% glucose; 1.6% galactose; 10.9% sucrose (108.67 mg/g); no melibiose or galactinol; 1.9% raffinose (18.64 mg/g) and 1.0% stachyose (9.70 mg/g). The pH of the soy protein product is 7.31. The product forms a thick consistency at 14% solids content in water and 90 degrees Celsius (° C.) and at 16% and 70° C.; a slight gel at 16% and 80° C. and a gel at 16% and 90° C. The product has a particle size distribution of: 60.7% retained on a number (#) 400 US standard sieve; 13.1% retained on a #200 and 0.8% retained on a #100.

EXAMPLE 3

An application of the soy protein product made in example 1 is a soy milk having 6.25 g of soy protein in a 24 g serving. A formula for such a beverage contains: 808.2 g water (80.82%); 62 g sugar (6.2%); 42.4 g soy protein product (4.24%); 38.6 g Cerestar USA, Inc. C*MD 01960 maltodextrin (3.86%); 27 g Cerestar USA C*DRY GL 01925 corn syrup (2.7%); 12 g gum arabic (1.2%); 5 g Central Soya Company, Inc. soybean oil (.5%); 2.5 g Central Soya CENTROLEX® F lecithin (0.25%); 1.8 g Na citrate (0.18%); 0.3 g Na phosphate dibasic (0.03%) and 0.02% antifoam agents. The dry ingredients are blended; pre-heated (140° F.) water added; antifoam added; high shear mixed/homogenized (2500 PSIG) and treated at ultra high temperature (285° F.) for 5 seconds.

The finished product was stable at neutral pH and had a good flavor similar to commercial soymilks. The most

TABLE

| Treatment | MONOSE % | SUCROSE % | RAFFINOSE % | STACHYOSE % | TOTAL SUGARS % | TOTAL RAFFINOSE & STACHYOSE % |
|---|---|---|---|---|---|---|
| Control, no enzyme | 1.0 | 10.3 | 1.2 | 8.1 | 20.6 | 9.3 |
| α-galactosidase 1 hour | 2.0 | 11.3 | 3.1 | 2.8 | 19.3 | 5.9 |
| α-galactosidase 2 hour | 2.2 | 12.0 | 2.4 | 1.1 | 17.7 | 3.6 |
| α-galactosidase 3 hour | 3.4 | 13.2 | 2.2 | 0.6 | 19.3 | 2.7 |
| α-galactosidase 4 hour | 4.2 | 14.7 | 1.7 | 0.2 | 20.8 | 1.9 | noticeable improvement in the product was in the mouthfeel. The beverage was smooth and free of grittiness compared to beverages made from currently available soy protein concentrates.

It will be understood that the claims are intended to cover all changes and modifications of the preferred embodiments of the invention herein chosen for the purpose of illustration which do not constitute a departure from the spirit and scope of the invention.

What is claimed is:

1. A soy protein product having (a) at least 60% protein of total dry matter; (b) a combined monosaccharide and sucrose content of at least 10% of total dry matter; (c) a combined raffinose and stachyose content of less than 5% of total dry matter and (d) being substantially free of galactinol, wherein the soy is not from low oligosaccharide soybeans.

2. The product of claim 1 wherein the product is an enzyme treated product.

3. The product of claim 2 wherein the enzyme is a α-glycosidase.

4. The product of claim 3 wherein the α-glycosidase is a α-glycosidase with essentially no invertase activity.

5. The product of claim 1 having less than 10% sucrose of total dry matter.

6. The product of claim 1 wherein the sucrose content is at least 10.5% of total dry matter and the monosaccharide content is about 2–3% of total dry matter.

7. A The product of claim 1 wherein the product has less than 1.5% stachyose of total dry matter and less than 2–3% raffinose of total dry matter.

8. The product of claim 1 wherein the product has less than 2% crude fiber of total dry matter.

9. The product of claim 1 having an isoflavone content greater than 2500 micrograms/gram of total dry matter and a sulfur-containing amino acid content greater than 2.2% of total amino acid content.

10. A liquid or dry beverage, food or nutritional product that uses the product of claim 1.

* * * * *